United States Patent
Park et al.

(10) Patent No.: US 10,426,864 B2
(45) Date of Patent: Oct. 1, 2019

(54) STORAGE APPARATUS HAVING AIR PURIFYING MODULE

(71) Applicant: SEOUL VIOSYS CO., LTD., Ansan-si (KR)

(72) Inventors: Jung Yeol Park, Ansan-si (KR); Young Hwan Son, Ansan-si (KR); Seong Min Lee, Ansan-si (KR); Jae Seon Yi, Ansan-si (KR); Jong Hyun Koo, Ansan-si (KR); Sang Hee Cho, Ansan-si (KR); Ju Won Yoo, Ansan-si (KR); Sung Lim Cho, Ansan-si (KR); Jong Rack Kim, Ansan-si (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 0 days.

(21) Appl. No.: 15/684,143

(22) Filed: Aug. 23, 2017

(65) Prior Publication Data
US 2017/0348456 A1    Dec. 7, 2017

Related U.S. Application Data

(63) Continuation of application No. 15/487,390, filed on Apr. 13, 2017, which is a continuation of application No. 14/445,254, filed on Jul. 29, 2014.

(30) Foreign Application Priority Data

Jul. 30, 2013    (KR) .................. 10-2013-0090512

(51) Int. Cl.
| | | |
|---|---|---|
| *A61L 9/20* | (2006.01) | |
| *B01D 46/00* | (2006.01) | |
| *F25D 17/04* | (2006.01) | |
| *A61L 9/16* | (2006.01) | |
| *F25D 11/00* | (2006.01) | |
| *F25D 17/06* | (2006.01) | |
| *F25D 27/00* | (2006.01) | |

(52) U.S. Cl.
CPC .............. *A61L 9/205* (2013.01); *A61L 9/16* (2013.01); *A61L 9/20* (2013.01); *B01D 46/0023* (2013.01);
(Continued)

(58) Field of Classification Search
CPC ............ F25D 17/042; F25D 17/062; F25D 2317/0415; F25D 2317/0417
See application file for complete search history.

(56) References Cited

U.S. PATENT DOCUMENTS 4,857,277 A * 8/1989 Broomfield ........... A23L 3/3409
422/186.07
5,078,971 A * 1/1992 Matuda .................... A61L 9/16
261/DIG. 88
(Continued)

FOREIGN PATENT DOCUMENTS

| CA | 2575998 A1 | 11/2007 |
| KR | 10-2007-0052144 A | 5/2007 |
| KR | 10-2007-0115086 A | 12/2007 |

OTHER PUBLICATIONS

Office Action in corresponding U.S. Appl. No. 15/487,390 dated Sep. 19, 2018.

*Primary Examiner* — Henry T Crenshaw
(74) *Attorney, Agent, or Firm* — Perkins Coie LLP

(57) ABSTRACT

A storage apparatus according to an embodiment may include a body having a storage space of storage products and an air purifying module coupled to the body. The air purifying module may include a light emitting diode part disposed along a passage of air to provide ultraviolet light, and a filter part disposed adjacent to the light emitting diode part.

18 Claims, 10 Drawing Sheets

(52) U.S. Cl.
CPC ..... *B01D 46/0028* (2013.01); *B01D 46/0036* (2013.01); *B01D 46/0038* (2013.01); *F25D 11/00* (2013.01); *F25D 17/042* (2013.01); *F25D 17/062* (2013.01); *F25D 27/00* (2013.01); *A61L 2209/12* (2013.01); *A61L 2209/14* (2013.01); *A61L 2209/22* (2013.01); *F25D 2317/0415* (2013.01); *F25D 2317/0417* (2013.01); *F25D 2317/06* (2013.01); *F25D 2317/067* (2013.01)

(56) References Cited

U.S. PATENT DOCUMENTS

| | | | | |
|---|---|---|---|---|
| 2004/0018125 | A1* | 1/2004 | Yang | A61L 9/205 |
| | | | | 422/186.3 |
| 2004/0041564 | A1* | 3/2004 | Brown | A61L 9/122 |
| | | | | 324/318 |
| 2006/0127288 | A1* | 6/2006 | Hay | A61L 9/014 |
| | | | | 422/186.3 |
| 2008/0112844 | A1* | 5/2008 | Garrett | A61L 9/205 |
| | | | | 422/4 |
| 2008/0168790 | A1* | 7/2008 | Hurlebaus | A61L 9/205 |
| | | | | 62/331 |
| 2008/0279733 | A1* | 11/2008 | Glazman | A61L 9/20 |
| | | | | 422/186.3 |
| 2011/0033346 | A1 | 2/2011 | Bohlen et al. | |
| 2012/0181911 | A1* | 7/2012 | Kim | A61L 2/14 |
| | | | | 312/405 |
| 2013/0015753 | A1* | 1/2013 | Son | F25D 29/00 |
| | | | | 312/405 |

* cited by examiner

STORAGE APPARATUS HAVING AIR PURIFYING MODULE

CROSS-REFERENCES TO RELATED APPLICATIONS

The present application is a continuation of U.S. patent application Ser. No. 15/487,390, filed Apr. 13, 2017, which is a continuation of U.S. patent application Ser. No. 14/445,254, filed Jul. 29, 2014, and further claims priority under 35 U.S.C. 119(a) to Korean Application No. 10-2013-0090512, filed on Jul. 30, 2013, in the Korean Intellectual Property Office, which is herein incorporated by reference in its entirety.

BACKGROUND

1. Technical Field

Exemplary embodiments of the present disclosure relate to storage apparatuses, and more particularly, to a storage apparatus having an air purifying module.

2. Related Art

Harmful bacteria may exist in horticultural products such as vegetables or fruits or various agricultural and livestock products, during production and distribution. For this reason, the bacteria may be increased or odor may be caused due to generation of putrefaction during distribution or refrigeration of the products. In this case, even if odor sources are removed, odor may remain in storage apparatuses such as refrigerators.

In recent years, technologies for removing bacteria or odor remaining in the storage apparatuses have been proposed. Specifically, a technology using an ultraviolet lamp for sterilization and deodorization has been disclosed, but the ultraviolet lamp has a risk of damage due to impact. In addition, a technology using an ion generating device for sterilization and deodorization has been disclosed, but the ion generating device may generate harmful ozone. Accordingly, air purifying technologies having high durability and improved sterilization and deodorization efficiency have been continuously required in the related industry.

SUMMARY

This summary is intended to provide an overview of the subject matter of this patent, and is not intended to identify essential elements or key elements of the subject matter, nor is it intended to be used to determine the scope of the claimed embodiments. The proper scope of this patent may be ascertained from the claims set forth below in view of the detailed description below and the drawings.

An embodiment of the present disclosure relates to a storage apparatus having an air purifying module capable of efficiently performing sterilization and deodorization functions when storage products requiring freshness, such as agricultural and livestock products, are kept in the storage apparatus.

In one embodiment, a storage apparatus may include a body having a storage space of storage products and an air purifying module coupled to the body. The air purifying module may include a light emitting diode part disposed along a passage of air to provide ultraviolet light, and a filter part disposed adjacent to the light emitting diode part.

In another embodiment, a storage apparatus may include a body including a storage chamber for storage of storage products and an air circulation conduit through which cold air is circulated to the storage chamber, and an air purifying module disposed within the air circulation conduit. The air purifying module may include a light emitting diode part disposed along a passage of air to provide ultraviolet light, and a filter part disposed adjacent to the light emitting diode part.

In another embodiment, a refrigerator may include storage chambers for storage of storage products, an air circulation conduit disposed in a space between the storage chambers, cold air being supplied to the storage chambers through the air circulation conduit, and an air purifying module disposed on an inner wall adjacent to a cold air outlet of the air circulation conduit to perform sterilization and deodorization functions. The air purifying module may include a filter part having a photocatalytic filter and a collection filter, and a light emitting diode part emitting ultraviolet light reacting with the filter part.

In a further embodiment, a refrigerator may include storage chambers for storage of storage products, an air circulation conduit disposed in a space between the storage chambers, cold air being supplied to the storage chambers through the air circulation conduit, and an air purifying module disposed within the air circulation conduit to perform sterilization and deodorization functions. The air purifying module may include a filter part having a photocatalytic filter and a collection filter, and a light emitting diode part emitting ultraviolet light reacting with the filter part.

BRIEF DESCRIPTION OF THE DRAWINGS

The above and other aspects, features, and other advantages will be more clearly understood from the following detailed description taken in conjunction with the accompanying drawings, in which.

DETAILED DESCRIPTION OF EMBODIMENTS

Figure 1:
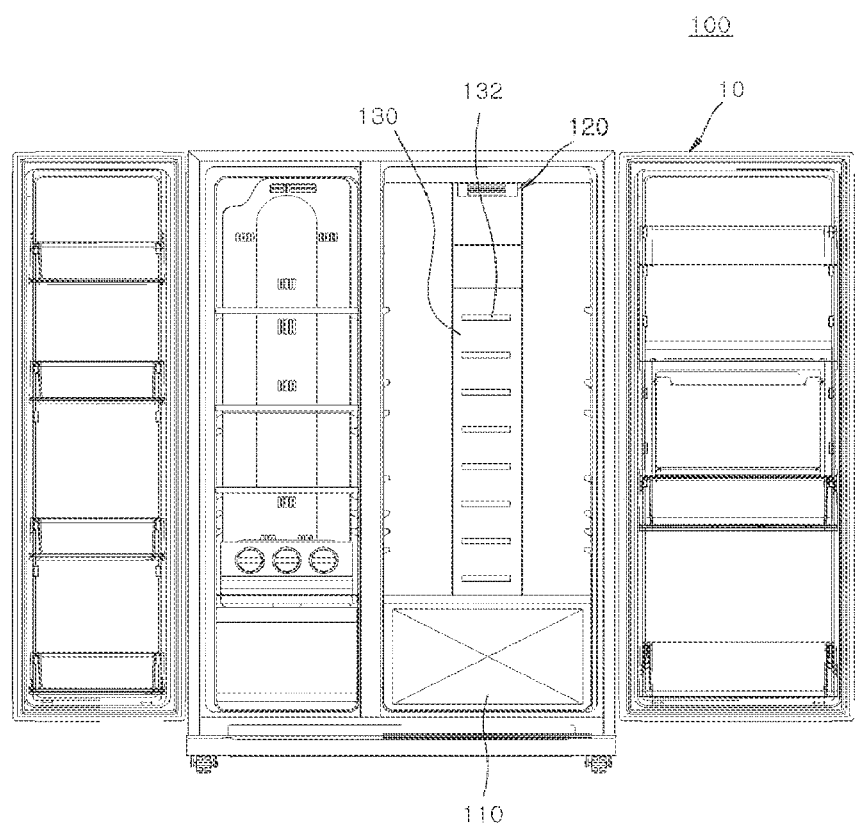
FIG. 1 is a schematic diagram illustrating a storage apparatus according to an embodiment of the present disclosure.

Hereinafter, embodiments of the present disclosure will be described with reference to accompanying drawings.

However, the embodiments are for illustrative purposes only and are not intended to limit the scope of the disclosure. For clarity, the detailed descriptions herein describe certain exemplary embodiments, but the disclosure in this application may be applied to any storage apparatus comprising certain of the features described herein and recited in the claims. In particular, although the following detailed description describes certain exemplary embodiments of storage apparatus, it should be understood that other embodiments may have different structures, forms, and configurations. The drawings may not be to scale, and the widths, lengths, and thicknesses shown may be exaggerated for clarity.

In addition, unless stated otherwise, terms such as "first" and "second" in the specification of the present disclosure are used to arbitrarily distinguish between the elements such terms describe. Thus, these terms are not necessarily intended to indicate temporal or other prioritization of such elements. In addition, terms such as "on," "above," "below," and "adjacent" as used herein refer to a position of one element relative to other elements. As such, an element disposed on, above, or below another element may be directly in contact with the other element or it may include one or more intervening elements. It will be understood that when an element is referred to as being "connected" or "installed" to another element, it can be directly connected or installed to the other element or intervening elements may also be present. In contrast, when an element is referred to as being "directly connected" or "directly installed" to another element, there are no intervening elements present. Throughout the disclosure, like reference numerals refer to like parts throughout the various figures and embodiments of the present disclosure.

FIG. 1 is a view schematically illustrating a storage apparatus according to an embodiment of the present disclosure. Although FIG. 1 shows a refrigerator as the storage apparatus, the present disclosure is not limited thereto. For example, the present disclosure may be applied to another storage apparatus including components to be described below.

Referring to FIG. 1, a storage apparatus, which is designated by reference numeral 100, may include a body 10 defining a frame of the storage apparatus 100. The body 10 may include a storage chamber 110 for providing a storage space of storage products and an air circulation conduit 130 through which cold air is supplied to the storage chamber 110. In addition, although not shown in FIG. 1, the storage apparatus 100 may include a compressor, a condenser, and an evaporator such that cold air may be supplied into the body 10. The compressor compresses refrigerant so that the refrigerant may be converted into a high-temperature and high-pressure gaseous state. The gaseous refrigerant discharged from the compressor is introduced into the condenser. In the condenser, the refrigerant is liquefied by radiating heat to be converted into a high-pressure liquid state. The high-pressure refrigerant discharged from the condenser may be converted into a low-pressure and low-temperature liquid state while passing through a capillary tube and then be introduced into the evaporator. In the evaporator, the low-pressure and low-temperature liquid refrigerant is converted into a gaseous state by absorbing heat around the evaporator, thereby enabling ambient air to be cooled. The air circulation conduit 130 may allow the cooled air to be circulated within the body 10. The air circulation conduit 130 may be formed with cold air outlets 132 and the cooled air may be supplied to the storage chamber 110 through the cold air outlets 132. In addition, the evaporated refrigerant may be introduced into the compressor and is then compressed to be converted into a high-temperature and high-pressure gaseous state. Through repetition of such a process, the inside of the body 10 may be cooled. The structure and arrangement of the compressor, condenser, and evaporator may depend on a configuration of the refrigerator.

An air purifying module 120 may be coupled to the body 10. In accordance with an embodiment, the air purifying module 120 may be coupled so as to be attachable to an inner wall of the body 10. Specifically, as shown in the FIG. 1, the air purifying module may be disposed on a ceiling of the refrigerator. In addition, the air purifying module 120 may be arranged adjacent to the cold air outlets 132 of the air circulation conduit 130 so that air may be easily introduced into the air purifying module 120.

The air purifying module 120 may include a light emitting diode part providing ultraviolet light and a filter part disposed adjacent to the light emitting diode part. The light emitting diode part and the filter part may be arranged along an air passage. The filter part may include a photocatalytic filter and a collection filter. The light emitting diode part may include light emitting diodes for photocatalysis, which act with the photocatalytic filter, and light emitting diodes for sterilization, which remove bacteria captured by the collection filter. Consequently, the air purifying module 120 may sterilize and deodorize air in the storage apparatus 100. Detailed configurations and functions of the air purifying module 120 will be described below.

Figure 2:
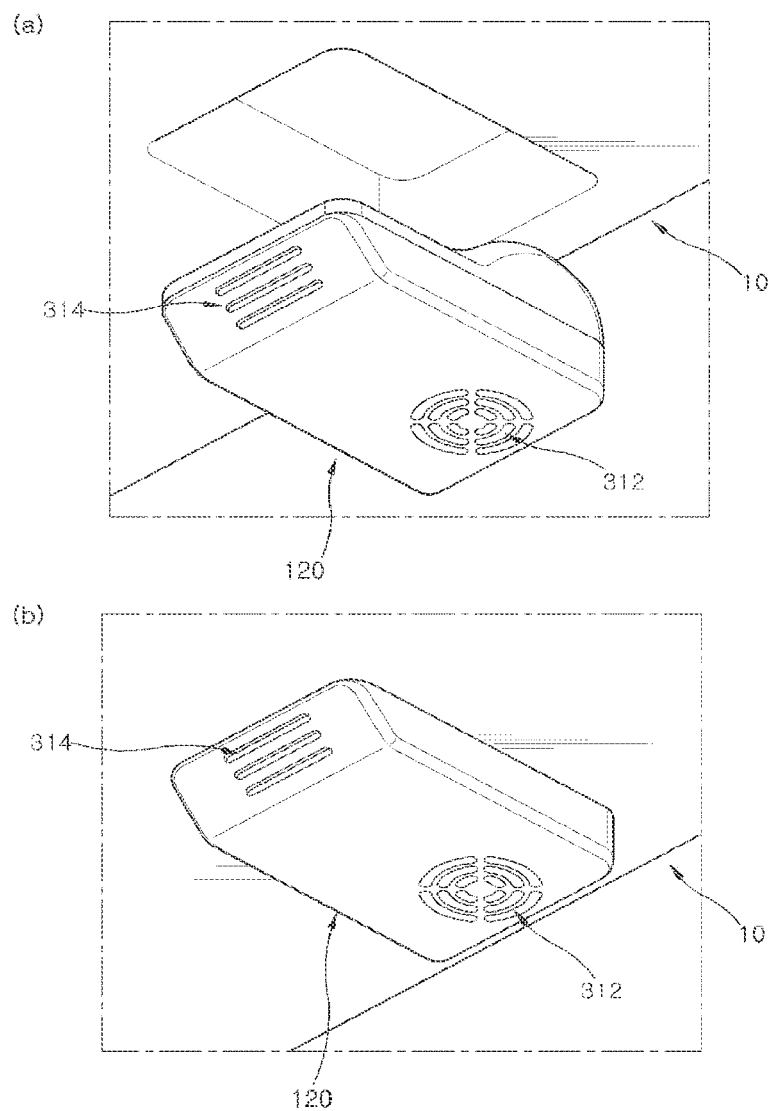
FIG. 2 is a schematic diagram illustrating a method of attaching an air purifying module according to an embodiment of the present disclosure.

FIG. 2 is a view schematically illustrating a method of attaching the air purifying module according to an embodiment of the present disclosure. Specifically, as shown in portions (a) and (b) of FIG. 2, the air purifying module 120 may be attached to one wall surface or a ceiling of the body 10. Air introduced through an air inlet 312 may be sterilized or deodorized within the air purifying module 120 and then be discharged through an air outlet 314. Although the air inlet 312 and the air outlet 314 are arranged to be directed in different directions within the body 10 as shown in FIG. 2, the present disclosure is not limited thereto. For example, the air inlet 312 and the air outlet 314 may be arranged in various forms.

Figure 3:
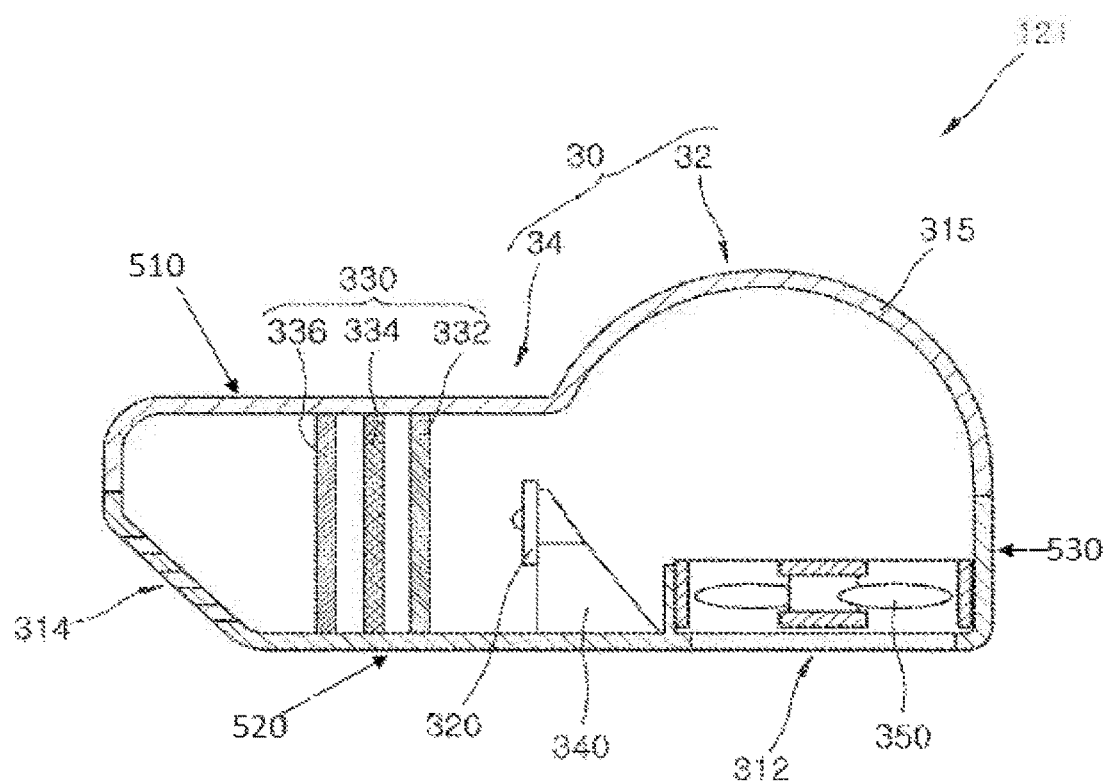
FIG. 3 is a schematic diagram illustrating a cross-sectional view of an air purifying module according to a first embodiment of the present disclosure.

FIG. 3 is a cross-sectional view schematically illustrating an air purifying module according to a first embodiment of the present disclosure. Referring to FIG. 3, an air purifying module, which is designated by reference numeral 121, may include a case 30, a light emitting diode part 320, and a filter part 330. The case 30 may include an air inlet 312 and air outlet 314. The flow of air introduced through the air inlet 312 may be changed within the case 30, and the air may be discharged through the air outlet 314 in a purified state by sterilization and deodorization thereof. The case 30 may include a top surface 510, a bottom surface 520 opposite to the top surface, and a side surface 530 connecting the top surface 510 and the bottom surface 520. The side surface 530 is connected to the top surface 510 through a corner which is non-straight, e.g., curved or rounded.

The case 30 may include a first case portion 32 adjacent to the air inlet 312 and a second case portion 34 adjacent to the air outlet 314. The first case portion 32 may include a circulation fan 350 disposed at the air inlet 312 for introduction of air into the case 30. In addition, the first case portion 32 may include a side wall portion 315 which outwardly protrudes in order to change the flow of air introduced into the case 30. The protruded side wall portion 315 may be disposed at a side opposite to the air inlet 312. The protruded side wall portion 315 may be curved to reduce resistance of air on an inner wall surface of the first case portion 32. For example, the protruded side wall portion 315 may have a hemispherical shape.

The second case portion 34 may include the light emitting diode portion 320 and the filter portion 330, which may be arranged along the flow of air in the case 30. The light emitting diode portion 320 may be arranged to be coupled to a heat sink 340 disposed at a side wall of the second case portion 34. The heat sink 340 may be made of a material having high thermal conductivity so as to rapidly conduct heat generated by the light emitting diode part 320 to the outside of the case 30. The heat sink 340 may be made of, for example, a material including metal. In accordance with an embodiment, the filter part 330 may include a photocatalytic filter 332 and a collection filter 334. As shown in FIG. 3, the filter part 330 may further include a carbon filter 336 at a rear end of the collection filter 334.

The light emitting diode part 320 may include light emitting diodes for photocatalysis, which act with the photocatalytic filter 332, and light emitting diodes for sterilization, which remove bacteria captured by the collection filter 334. Each of the light emitting diodes for photocatalysis may emit for example, ultraviolet light of about 300 to 400 nm, and each of the light emitting diodes for sterilization may emit, for example, ultraviolet light of about 200 to 300 nm. In embodiments, the light emitting diodes may be classified as light emitting diodes for photocatalysis and light emitting diodes for sterilization, and may be arranged according to functions of the light emitting diodes. However, in some embodiments, such classifications may not apply, and the light emitting diodes may serve multiple functions. That is, the light emitting diodes for photocatalysis may also perform a sterilization function together, and the light emitting diodes for sterilization may also generate a photocatalytic reaction together with the photocatalytic filter.

A method of operating the air purifying module in the above-mentioned first embodiment will be described. The circulation fan 350 of the first case portion 32 may be operated such that air, which is a target to be purified, may be introduced from the air inlet 312. After the flow of the introduced air is changed through the side wall portion 315, the air may move to the second case portion 34. The air may be sterilized—including removing, killing, or otherwise inactivating bacteria in the air—by ultraviolet light emitted from the light emitting diodes for sterilization, while the air is moved into the second case portion 34. In addition, the bacteria in the air may be captured by the collection filter 334 and then be removed by ultraviolet light emitted from the light emitting diodes for sterilization. The collection filter 334 may capture bacteria in moving air and thus help increase the sterilization efficiency of the sterilization light emitting diodes. That is, the collection filter 334 may increase a time for which bacteria are exposed to ultraviolet light for sterilization during moving in the air purifying module 121. The collection filter 334 may be, for example, a cabin filter.

In addition, odor in moving air may be removed by a photocatalytic reaction between ultraviolet light emitted from the light emitting diodes for photocatalysis and the photocatalytic filter 332. In addition, when moving air passes through the rear carbon filter 336, odor of the air may be further removed. Although not shown in FIG. 31 the filter part 330 may further include a variety of commercially functional filters.

Figure 4:
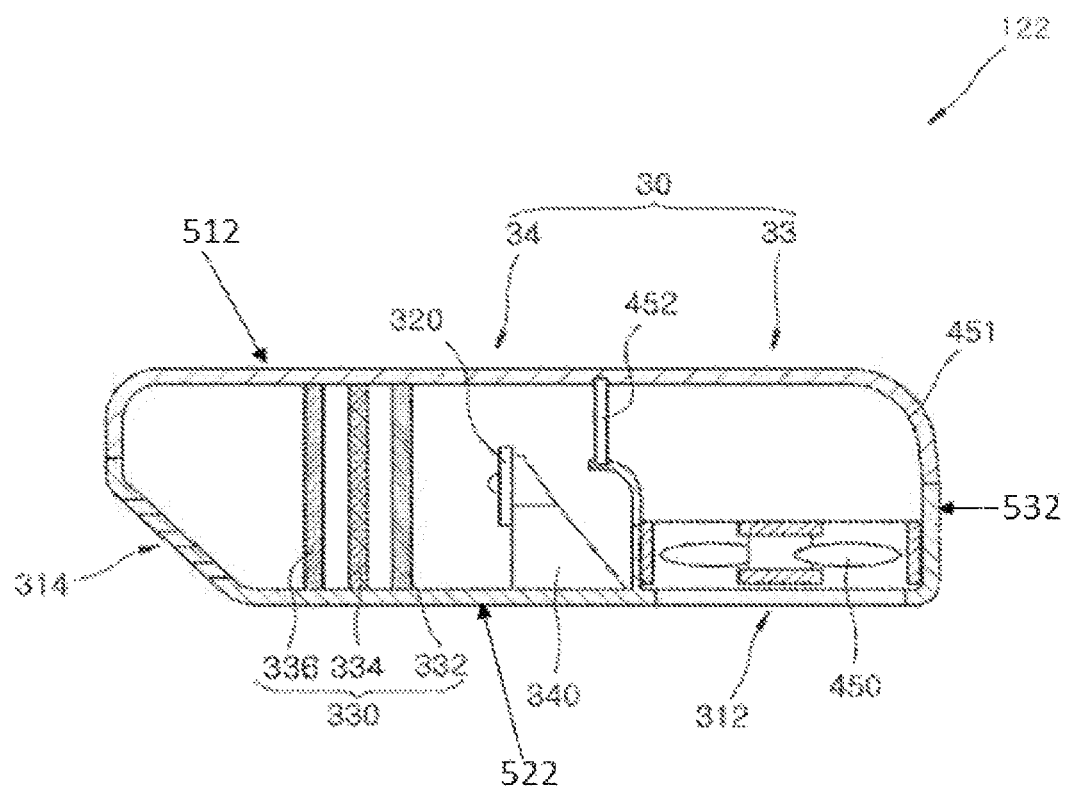
FIG. 4 is a schematic diagram illustrating a cross-sectional view of an air purifying module according to a second embodiment of the present disclosure.

FIG. 4 is a cross-sectional view schematically illustrating an air purifying module according to a second embodiment of the present disclosure. Referring to FIG. 4, an air purifying module, which is designated by reference numeral 122, may be substantially identical to the above-mentioned air purifying module 121 in FIG. 3, except that a first case portion 33 has a different configuration. Accordingly, to avoid a repetitive description, only the different configuration will be mainly described below. The case 30 may include a top surface 512, a bottom surface 522 opposite to the top surface, and a side surface 532 connecting the top surface 512 and the bottom surface 522. The side surface 532 is connected to the top surface 512 through a corner which is non-straight, e.g., curved or rounded.

Referring to FIG. 4, the first case portion 33 may include a circulation fan 450, which may be disposed at an air inlet 312 and may have a conduit 451 capable of allowing the flow of air to be changed. In FIG. 4, since the conduit 451 allows the flow of introduced air to be changed in a substantially perpendicular direction, the air may flow to a second case portion 34 through a discharge part 452. The circulation fan 450 may be, for example, a commercial blower fan. Since the circulation fan 450 has the conduit 451, the first case portion 33 may not have the side wall portion 315 of FIG. 3. As such, if the circulation fan 450 has various conduits allowing the flow of air to be changed, various modified examples may be applied to the circulation fan 450.

Figure 5:
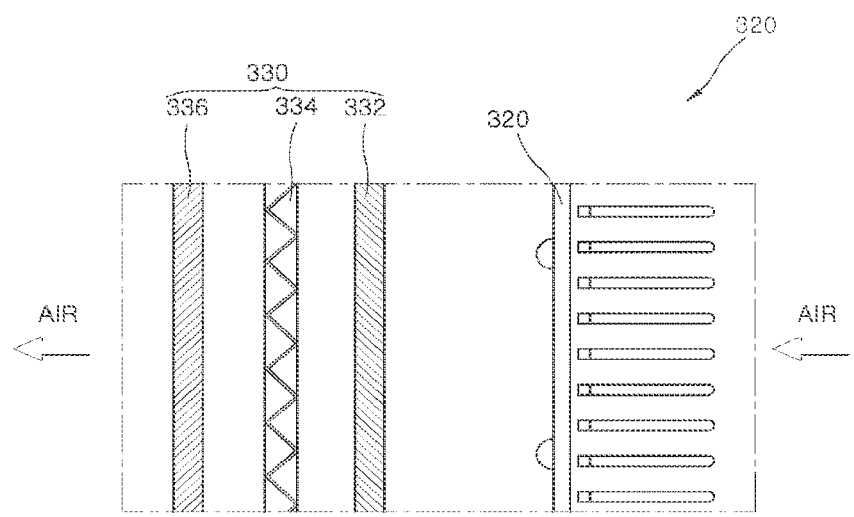
FIG. 5 is a schematic diagram illustrating a cross-sectional view of a light emitting diode part and a filter part according to an embodiment of the present disclosure.
Figure 6:
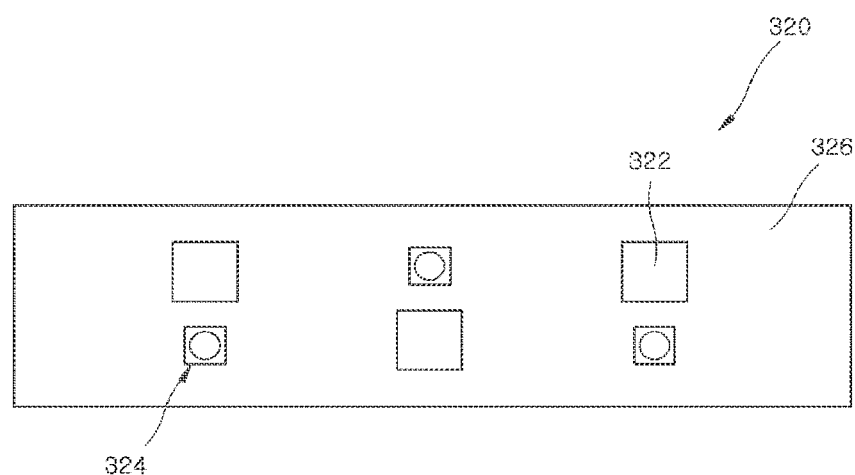
FIG. 6 is a schematic diagram illustrating a top view of a light emitting diode part according to an embodiment of the present disclosure.

FIG. 5 is a cross-sectional view schematically illustrating a light emitting diode part and a filter part according to an embodiment of the present disclosure. FIG. 6 is a top view schematically illustrating the light emitting diode part according to an embodiment of the present disclosure. Referring to FIG. 5, the light emitting diode part 320 is arranged to emit ultraviolet light in the substantially same direction as the flow of air in the second case portion 34 of the first or second embodiment of the present disclosure. As shown in FIG. 6, the light emitting diode part 320 may include light emitting diodes for sterilization 322 and light emitting diodes for photocatalysis 324. Each of the light emitting diodes for sterilization 322 may emit ultraviolet light of about 200 to 300 nm, and each of the light emitting diodes for photocatalysis 324 may emit ultraviolet light of about 300 to 400 nm. The light emitting diodes for sterilization 322 and the light emitting diodes for photocatalysis 324 may be selectively turned on by control of a control unit (not shown) to emit light. On the contrary, the light emitting diodes for sterilization 322 and the light emitting diodes for photocatalysis 324 may also be controlled so as to simultaneously emit light.

Referring to FIG. 6 again, although the light emitting diodes for sterilization 322 and the light emitting diodes for photocatalysis 324 may be alternately arranged on a support member 326, the present disclosure is not limited thereto. For example, the light emitting diodes for sterilization 322 and the light emitting diodes for photocatalysis 324 may be arranged in various forms. That is, the light emitting diodes for sterilization 322 may be arranged in a row and the light emitting diodes for photocatalysis 324 may be arranged in a row. In addition, regions in which the light emitting diodes for sterilization 322 are present and regions in which the light emitting diodes for photocatalysis 324 are present may also be separately arranged in a partitioned manner.

Referring to FIG. 5 again, the light emitting diode part 320 may be disposed such that the direction of ultraviolet light emitted from the light emitting diodes for sterilization 322 and light emitting diodes for photocatalysis 324 of the light emitting diode part 320 substantially coincides with the flow direction of air in the air purifying module 121 or 122. The filter part 330 may include a photocatalytic filter 3321 a collection filter 334, and a carbon filter 336, which are sequentially arranged from the light emitting diode part 320.

The photocatalytic filter 332 may be a photocatalytic medium and include a substance providing a photocatalytic reaction. For example, the photocatalytic medium may include a titanium oxide (TiO2), a silicon oxide (SiO2), a tungsten oxide (WO3), or a zirconium oxide (ZnO). The photocatalytic filter 332 may be formed in a layered structure including a titanium oxide (TiO2). The photocatalytic filter 332 may be manufactured by a layer coated with a material such as metal foam or porous metal through which air may flow.

The photocatalytic filter 332 may perform a photocatalytic reaction with ultraviolet light of about 300 to 400 nm emitted from the light emitting diodes for photocatalysis 324. When the ultraviolet light is absorbed into the photocatalytic medium, electrons (e−) and holes (+) may be generated on a surface of the photocatalytic medium and, as such, the electrons may react with oxygen on the surface of the photocatalytic medium to generate superoxide anions (O2−). In addition, the holes may react with moisture present in air to generate hydroxyl radicals (OH—). In this case, the generated hydroxyl radicals may oxidize and decompose organic substances. Consequently, containments and odor substances in air introduced into the air purifying module may be decomposed and converted into water and carbon dioxide. Therefore, the photocatalytic filter 332 may deodorize introduced air by cooperating with the light emitting diodes for photocatalysis 324.

The collection filter 334 may perform a function of capturing bacteria in introduced air. To that end, the collection filter 334 may have fine pores such that bacteria do not easily pass through the collection filter 334. In order to increase a surface area of the collection filter 334 to increase a captured amount per unit area, the collection filter 334 may include a filter substance having a folded shape in the flow direction of air as shown in FIG. 5. Bacteria captured by the collection filter 334 may be sterilized by ultraviolet light of about 200 to 300 nm emitted from the light emitting diodes for sterilization 322. The collection filter 334 may increase a time for which bacteria in air are exposed to ultraviolet light for sterilization, thereby enhancing sterilization efficiency of the light emitting diodes for sterilization 322.

The carbon filter 336 may be disposed at a rear end of the collection filter 334. The carbon filter 336 may include activated carbon and a catalyst so that organic chemical substances in air are filtered out during passage through the carbon filter 336. Consequently, it may be possible to deodorize introduced air. In embodiments, by configuring the carbon filter 336 together with the photocatalytic filter 332 and the light emitting diodes for photocatalysis, it may be possible to enhance deodorization efficiency of an air purifying module. In addition, the carbon filter 336 may have relatively weak durability and short life. Therefore, by disposing the carbon filter 336 at the rear end of the photocatalytic filter 332, it may be possible to extend the life of the carbon filter 336.

Although not shown in FIG. 6, the filter part 330 may additionally include various functional filters. For example, the functional filters may include a high-efficiency particulate air (HEPA) filter, a deodorization filter, an antibacterial filter, an allergen filter, etc.

Figure 7:
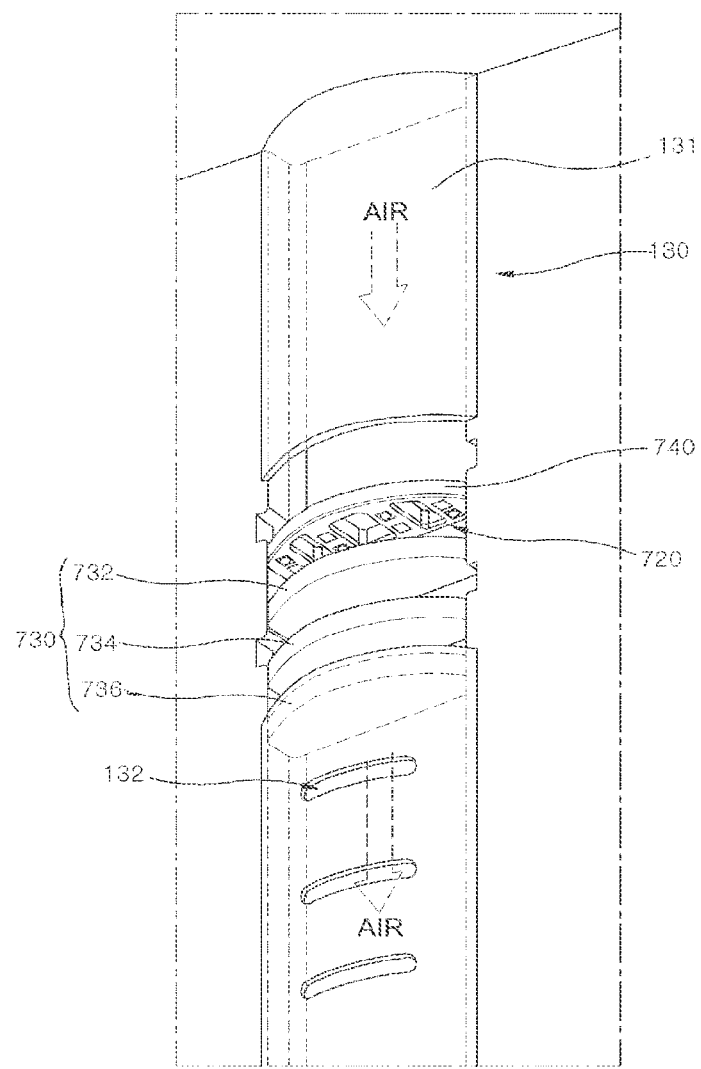
FIG. 7 is a schematic diagram illustrating an exemplary air circulation conduit to which an air purifying module according to an embodiment of the present disclosure may be mounted.
Figure 8:
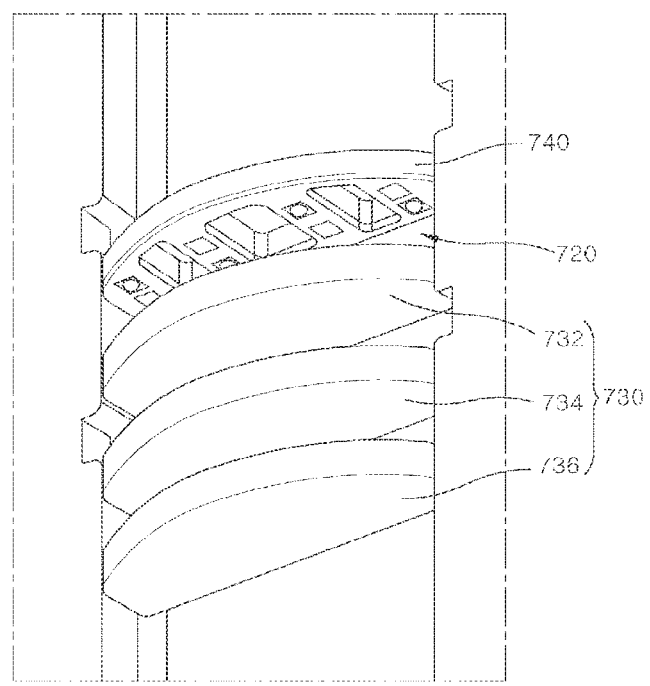
FIG. 8 is a schematic diagram illustrating an enlarged view of the air purifying module of FIG. 7.

FIG. 7 is a view schematically illustrating an air circulation conduit to which an air purifying module may be mounted, according to an embodiment of the present disclosure. An air purifying module may be disposed in the air circulation conduit 130 of the storage apparatus 100 described in FIG. 1. FIG. 8 is an enlarged view illustrating the air purifying module of FIG. 7.

Referring to FIG. 7, air circulation conduit 130 may have an inner space 131 in which air having a sufficient volume may flow. The air circulation conduit 130 may have cold air outlets 132 through which cold air may be supplied to a storage chamber.

Referring to FIGS. 7 and 8, an air purifying module may include a light emitting diode part 720 and a filter part 730, which may be arranged along an air passage in the inner space 131. The light emitting diode part 720 may be disposed on a heat sink 740 having openings through which air may flow. The heat sink 740, the light emitting diode part 720, and the filter part 730 may be attached to the air circulation conduit 130.

The filter part 730 may include a photocatalytic filter 732 and a collection filter 734, which are sequentially arranged from the light emitting diode part 720. In addition, the filter part 730 may further include a carbon filter 736, which is disposed at a rear end of the collection filter 734 and performs a deodorization function. Since the functions and configurations of the photocatalytic filter 732, collection filter 734, and carbon filter 736 are substantially identical to those of the photocatalytic filter 332, collection filter 334, and carbon filter 336 of the embodiments described in FIGS. 3 to 5, no detailed description will be given to avoid repetitive description.

The light emitting diode part 720 may include light emitting diodes for photocatalysis, which act with the photocatalytic filter 732, and light emitting diodes for sterilization, which remove bacteria captured by the collection filter 734. Each of the light emitting diodes for photocatalysis may emit, for example, ultraviolet light of about 300 to 400 nm, and each of the light emitting diodes for sterilization may emit, for example, ultraviolet light of about 200 to 300 nm. In embodiments, the light emitting diodes may be classified as light emitting diodes for photocatalysis and light emitting diodes for sterilization, and may be arranged according to functions of the light emitting diodes. However, in some embodiments, such classification may not apply, and the light emitting diodes may server multiple functions. That is, the light emitting diodes for photocatalysis may also perform a sterilization function together, and the light emitting diodes for sterilization may also generate a photocatalytic reaction together with the photocatalytic filter.

Figure 9:
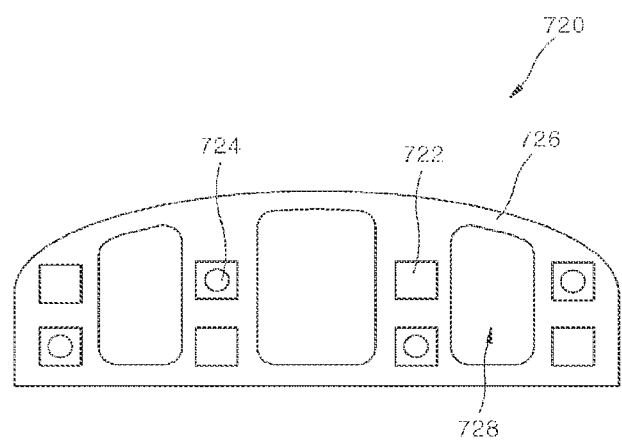
FIG. 9 is a schematic diagram illustrating a light emitting diode part according to an embodiment of the present disclosure.

FIG. 9 is a view schematically illustrating a light emitting diode part according to an embodiment of the present disclosure. Referring to FIG. 9, a light emitting diode part which is designated by reference numeral 720, may include light emitting diodes for sterilization 722 and light emitting diodes for photocatalysis 724, which may be arranged on a support member 726 having openings 728. Each of the openings 728 formed on the support member 726 may be formed at the same position as the associated opening of the heat sink 740, such that air may flow through the light emitting diode part 720 and heat sink 740.

Referring to FIG. 9 again, the light emitting diodes for sterilization 722 and the light emitting diodes for photocatalysis 724 may be arranged on the support member 726 while interposing the openings 728 therebetween. Although the respective light emitting diodes for sterilization 722 are paired with the respective light emitting diodes for photocatalysis 724, the present disclosure is not limited thereto. For example, the light emitting diodes for sterilization 722 and the light emitting diodes for photocatalysis 724 may be arranged in various forms. That is, a region in which a pair of light emitting diodes for sterilization 722 is present and a region in which a pair of light emitting diodes for photocatalysis 724 is present may be arranged, with interposing the opening 728 therebetween, in a partitioned manner.

Figure 10:
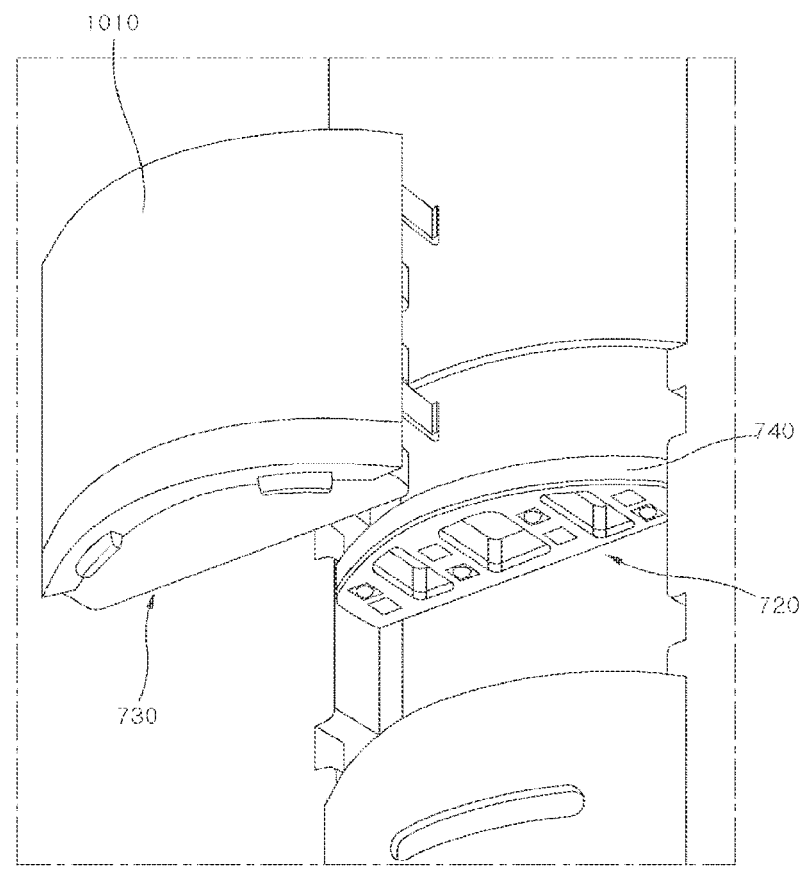
FIG. 10 is a schematic diagram illustrating a method of installing an air purifying module according to an embodiment of the present disclosure.

FIG. 10 is a view schematically illustrating a method of installing an air purifying module according to an embodiment of the present disclosure. Some components of an air purifying module may be installed so as to be detachably attachable to an air circulation conduit. Specifically, referring to FIG. 10, a filter part 730, which is periodically required for replacement, may be configured to be detachably attachable to the air circulation conduit. As shown in FIG. 10, the filter part 730 may be attached to a cover 1010 and the cover may be attached to the circulation conduit. Consequently, end-of-life filters may be easily replaced.

As is apparent from the above description, embodiments of the present disclosure may provide a storage apparatus capable of enhancing freshness and storability of storage products by providing an air purifying module that enables the storage products requiring freshness to be efficiently sterilized and deodorized.

Ultraviolet light emitting diodes applied for sterilization and deodorization functions in embodiments of the present disclosure have an advantage of miniaturization and high durability compared to conventional ultraviolet lamps using thermal electrons and luminescent substances. In addition, the ultraviolet light emitting diodes may have long life due to characteristics of light emitting diodes.

The embodiments of the present disclosure have been disclosed above for illustrative purposes. Those skilled in the art will appreciate that various modifications, additions, and substitutions are possible, without departing from the scope and spirit of the inventive concept as disclosed in the accompanying claims, and their equivalents.

Further, in describing embodiments, the specification may have presented methods and/or processes as particular sequences of steps. However, to the extent that the methods or processes do not rely on the particular order of steps set forth herein, the methods or processes should not be limited to the particular sequences of steps described. As one of ordinary skill in the art would appreciate, other sequences of steps may be possible. Therefore, the particular order of the steps set forth in the specification should not be construed as limitations on the claims. In addition, the claims directed to the methods and/or processes should not be limited to the performance of their steps in the order written and one skilled in the art can readily appreciate that the sequences may be varied.

What is claimed is:

1. An air purifying system including,
   a case having a top surface that is flat, a bottom surface opposite to the top surface, and a side surface connecting the top surface and the bottom surface;
   an air inlet arranged on the bottom surface to introduce an air from an exterior of the case to an interior of the case;
   a circulation fan arranged inside the case and disposed to receive the air from the air inlet and to generate an air flow moving in a first direction, wherein the top surface of the case is connected to the side surface though a rounded corner structured to cause at least a portion of the generated air flow to change an air flow direction to a second direction, the air moving in the second direction along the top surface,
   a light emitting diode part arranged above the air inlet and including a light emitting diode positioned to sterilize the air flow moving in the second direction;
   an air outlet positioned to discharge the air to the exterior of the case; and
   a collection filter arranged in the case and configured to capture bacteria to increase a sterilization efficiency of the air purifying system,
   wherein the first direction is toward the top surface and the second direction is substantially perpendicular to the first direction.

2. The air purifying system of claim 1, further including:
   a filter part inside the case and operable to sterilize or deodorize the air flow moving inside the case.

3. The air purifying system of claim 2, wherein the filter part includes at least one of a photocatalytic filter, a collection filter, or a carbon filter.

4. The air purifying system of claim 2, wherein the light emitting diode part emits ultraviolet light to kill bacteria captured in the case.

5. The air purifying system of claim 3 wherein the filter part includes a photocatalytic filter and wherein the light emitting diode part emits ultraviolet light to activate the photocatalytic filter.

6. The air purifying system of claim 1, wherein the light emitting diode part is arranged between the circulation fan and the air outlet.

7. The air purifying system of claim 1, wherein the light emitting diode part is arranged to emit light toward the air flow generated in the circulation fan and moving in the second direction.

8. The air purifying system of claim 1, wherein the air outlet is arranged on another side surface connecting the top surface and the bottom surface and facing the side surface and configured to discharge the air through the side surface.

9. An air purifying system including:
   a case having a top surface that is flat, a bottom surface opposite to the top surface, and a side surface connecting the top surface and the bottom surface and providing an interior for an air flow to flow, the side surface having a non-straight portion forming a corner of the side surface;
   an air inlet formed on the bottom surface to introduce an air from an exterior of the case to the interior;
   a circulation fan arranged inside the case and disposed to receive the air from the air inlet and to generate an air flow moving in a first direction, wherein the top surface of the case is connected to the side surface through the corner of the side surface structured to cause at least a portion of the generated air flow to change an air flow direction to a second direction, the top surface structured to allow the air to move in the second direction;
   an air outlet arranged on another side surface of the case and discharging the air to the exterior of the case through another side surface;
   a filter part formed between the air inlet and the air outlet and operable to sterilize or deodorize the air flowing inside the case, wherein the filter part includes at least one of a collection filter, or a deodorizing filter; and
   a light emitting diode part arranged between the air inlet and the air outlet and providing ultraviolet light toward the air introduced to the interior and at least one of the collection filter, or the deodorizing filter.

10. The air purifying system of claim 9, wherein the light emitting diode part emits ultraviolet light to remove kill bacteria captured in the case.

11. The air purifying system of claim 9, wherein the light emitting diode part emits ultraviolet light to activate the photocatalytic filter.

12. The air purifying system of claim 9, wherein the air circulation fan is arranged between the air inlet and the air outlet.

13. The air purifying system of claim 12, wherein the air flowing inside the case flows in a first direction and a second direction that are different from each other.

14. The air purifying system of claim 12, wherein the first direction is toward a top surface of the case and the second direction is substantially perpendicular to the first direction.

15. The air purifying system of claim 12, wherein the light emitting diode part is arranged to emit light toward the air flow generated in the circulation fan and moving in the second direction.

16. An air purifying system including:
a case having a top surface that is flat, a bottom surface opposite to the top surface, and side walls connecting the top surface and the bottom surface and providing an interior for an air flow to flow, the side walls including a first side wall and a second side wall and the first side wall having a non-straight portion forming a corner of the first side wall and structured to cause at least a portion of the air flow to change an air flow direction through the corner of the first side wall;
an air inlet formed on the bottom surface to introduce an air from an exterior of the case to the interior;
an air outlet arranged on the second side wall of the case and discharging the air to the exterior of the case through the sidewall;
a filter part formed between the air inlet and the air outlet and operable to sterilize or deodorize the air flowing inside the case, wherein the filter part includes a collection filter and a deodorizing filter; and
a light emitting diode part arranged between the air inlet and the air outlet and providing ultraviolet light toward the air introduced to the interior and at least one of the collection filter, or the deodorizing filter, wherein the light emitting diode part is located closer to the deodorizing filter than the collection filter.

17. The air purifying system of claim 16, further comprising a circulation fan arranged inside the case and disposed to receive the air from the air inlet and to generate an air flow moving in a first direction, wherein the case causes at least a portion of the generated air flow to change direction and move in a second direction.

18. The air purifying system of claim 16, wherein the first direction is toward the top surface and the second direction is substantially perpendicular to the first direction.

* * * * *